(12) United States Patent
Hwang

(10) Patent No.: US 7,334,478 B2
(45) Date of Patent: Feb. 26, 2008

(54) DEVICE FOR GUIDING THE MOVEMENT OF A TRANSDUCER OF AN ULTRASONIC PROBE

(75) Inventor: Won Soon Hwang, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 150 days.

(21) Appl. No.: 11/267,507

(22) Filed: Nov. 7, 2005

(65) Prior Publication Data

US 2007/0012114 A1    Jan. 18, 2007

(30) Foreign Application Priority Data

Jul. 15, 2005    (KR) ............... 10-2005-0064278

(51) Int. Cl.
  *G01N 29/04* (2006.01)
  *A61B 8/00* (2006.01)
(52) U.S. Cl. .............. 73/618; 73/625; 73/635; 600/447; 600/459
(58) Field of Classification Search .......... 73/618, 73/625, 635, 636; 600/444, 447, 459
See application file for complete search history.

(56) References Cited

U.S. PATENT DOCUMENTS

| 4,120,291 A | 10/1978 | Paton et al. |
| 5,460,179 A | 10/1995 | Okunuki et al. |
| 7,066,889 B2 * | 6/2006 | Taylor .................. 600/459 |
| 7,081,093 B2 * | 7/2006 | Flesch .................. 600/459 |
| 2007/0016060 A1 * | 1/2007 | Hwang .................. 600/459 |

FOREIGN PATENT DOCUMENTS

CH    693648 A5    11/2003

OTHER PUBLICATIONS

U.S. Appl. No. 11/267,507, filed Nov. 7, 2005, Hwang.
U.S. Appl. No. 11/266,325, filed Nov. 4, 2005, Hwang.

* cited by examiner

*Primary Examiner*—Herzon Williams
*Assistant Examiner*—Jacques M. Saint-Surin
(74) *Attorney, Agent, or Firm*—Oblon, Spivak, McClelland, Maier & Neustadt, P.C.

(57) ABSTRACT

The present invention relates to a device for guiding the movement of a transducer of an ultrasonic probe in an ultrasonic diagnostic apparatus for acquiring a 3-dimensional ultrasound image. A pair of guide rails is disposed near both side-ends of the transducer and is disposed apart therefrom by predetermined gaps. Slots are formed lengthwise at side surfaces of the guide rails. Each slot has a bottom wall and a side wall. Bearings coupled to the both side-ends of the transducer are received in the slots and roll on the bottom walls of the slots. First magnets are fixed to the both side-ends of the transducer and second magnets are fixed to the side walls of the slots along the overall length of the slots. The first magnets are received in the slots and are disposed opposite to the second magnets so that repulsive forces are generated therebetween.

4 Claims, 3 Drawing Sheets

DEVICE FOR GUIDING THE MOVEMENT OF A TRANSDUCER OF AN ULTRASONIC PROBE

FIELD OF THE INVENTION

The present invention generally relates to an ultrasonic probe, and more particularly to a device for guiding the movement of a transducer of an ultrasonic probe in an ultrasonic diagnostic apparatus for acquiring a 3-dimensional ultrasound image.

BACKGROUND OF THE INVENTION

An ultrasonic diagnostic apparatus is a medical equipment for obtaining an ultrasound image of a target region in an object so as to provide clinical information of the target region, such as lesion or neoplasm information of internal organs, fetus information and the like. Typically, the ultrasonic diagnostic apparatus comprises at least one probe for radiating an ultrasonic wave to the target region and receiving an echo signal reflected from the target region. The probe has a transducer for converting an ultrasonic signal into an electric signal.

Recently, certain techniques for acquiring a 3-dimensional (3D) ultrasound image by moving the transducer have been developed to obtain more accurate diagnosis.

FIG. 1 is a perspective view schematically showing an inner structure of a prior art ultrasonic probe. FIG. 2 is a perspective view showing a device for guiding the movement of a transducer of a prior art ultrasonic probe.

As shown in the drawings, a prior art ultrasonic probe is equipped with a transducer 10 for converting an ultrasonic signal into an electric signal, a motor 30 for generating driving power for moving the transducer 10, and means for transmitting the power from the motor 30 to the transducer 10. Such components are mounted to a supporting frame 20, which is contained in a housing (not shown).

The supporting frame 20 includes rectangular verges at its upper portion. A pair of guide rails 22 is mounted on the opposing verges of the supporting frame 20 such that the transducer 10 is positioned between the pair of guide rails 22. Slots 24 are formed lengthwise at the side surfaces of the guide rails 22 opposite to both side-ends of the transducer 10. Each slot 24 has a side wall and a bottom wall.

Brackets 12, to which bearings 16 are rotatably mounted, are coupled to both side-ends of the transducer 10. Supporting shafts 14 for supporting the bearings 16 are fixed to the brackets 12. The supporting shafts 14 horizontally extend toward the slots 24 of the guide rails 22 and the bearings 16 are received within the slots 24. The brackets 12 are located apart from the side surfaces of the guide rails 22 by predetermined gaps in order to avoid any undesired friction therebetween. When the driving power of the motor 30 is transmitted to the transducer 10 by the power-transmitting means, the transducer 10 moves along the guide rails 22 while the bearings 16 roll on the bottom walls of the slots 24.

However, during the movement of the transducer, the transducer may rattle between the guide rails due to the operational vibration of the motor or a manufacturing or assembling error. Thus, a friction may occur between the side surfaces of the guide rails and the bearing-supporting brackets. Such a friction causes operational noises or vibrations, and may further cause wears or deformations of the components. Further, the transducer moves somewhat roughly by the friction and the ultrasonic wave is radiated irregularly. As such, the image quality becomes degraded, which can cause an erroneous diagnosis.

SUMMARY OF THE INVENTION

It is an object of the present invention to provide a device for guiding the movement of a transducer of an ultrasonic probe, which can prevent the occurrence of an undesired friction between a transducer and guide rails, thereby moving the transducer smoothly and achieving a high image quality.

Consistent with the foregoing object and in accordance with the invention as embodied herein, there is provided a device for guiding the movement of a transducer of an ultrasonic probe, wherein the probe includes a transducer for converting an ultrasonic signal into an electric signal and a motor for generating driving power for moving the transducer. The device comprises: a pair of guide rails disposed adjacent to both side-ends of the transducer, the guide rails being apart from the both side-ends of the transducer by predetermined gaps; slots formed lengthwise at the side surfaces of the guide rails opposite to the both side-ends of the transducer, each slot having a bottom wall and a side wall; bearings coupled to the both side-ends of the transducer, the bearings being received in the slots and rolling on the bottom walls of the slots; and means for keeping the gaps constant between the both side-ends of the transducer and the guide rails.

In accordance with one aspect of the present invention, the means includes first magnets fixed to the both side-ends of the transducer and second magnets fixed to the side walls of the slots along the overall length of the slots. The first magnets are received within the slots and are disposed opposite to the second magnets so that repulsive forces are generated therebetween.

In accordance with another aspect of the present invention, the means is auxiliary bearings mounted to the both side-ends of the transducer. The auxiliary bearings are received within the slots and roll on the side walls of the slots.

The guide rails and the slots have a convex, linear or concave shape.

BRIEF DESCRIPTION OF THE DRAWINGS above and other objects and features of the present invention will become apparent from the following description of preferred embodiments given in conjunction with the accompanying drawings, in which.

DETAILED DESCRIPTION OF THE PRESENT INVENTION

Figure 3:
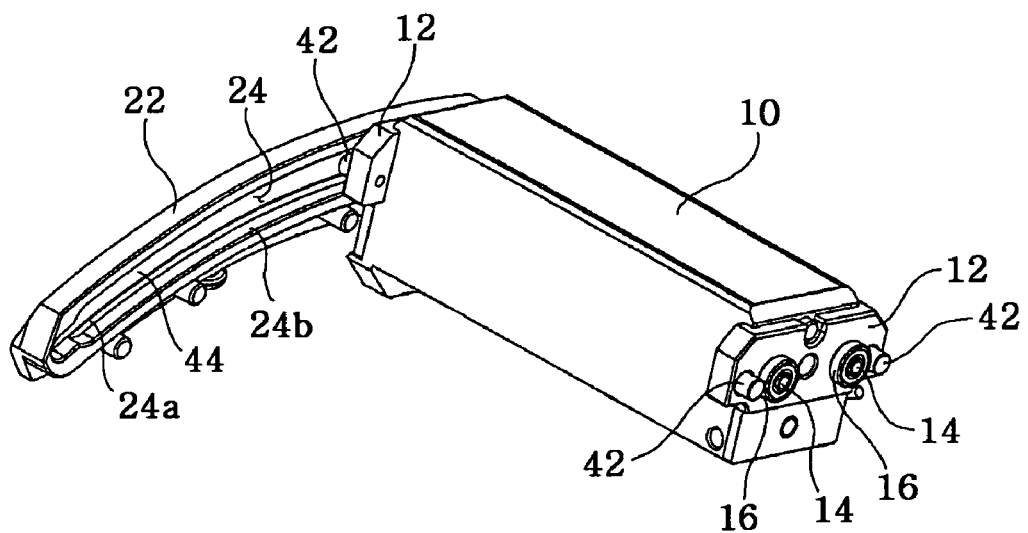
FIG. 3 is a perspective view showing a device for guiding the movement of a transducer of an ultrasonic probe constructed in accordance with a preferred embodiment of the present invention.
Figure 4:
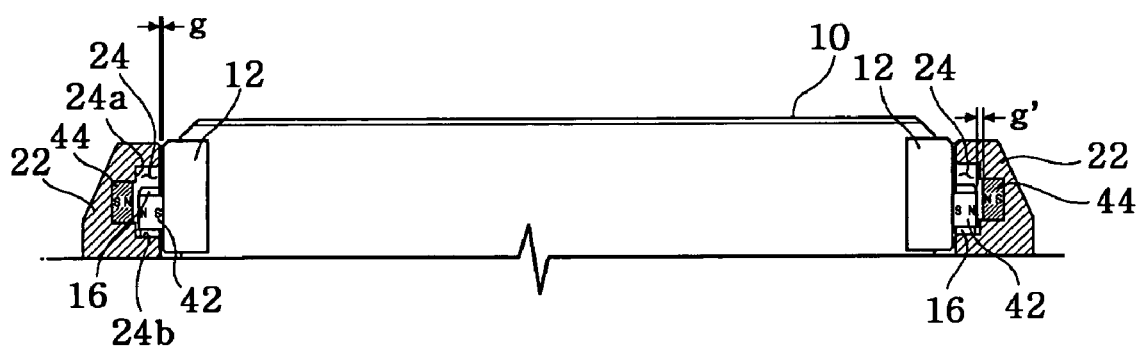
FIG. 4 is a partial sectional view of FIG. 3.

FIG. 3 is a perspective view showing a device for guiding the movement of a transducer of an ultrasonic probe constructed in accordance with a preferred embodiment of the present invention. FIG. 4 is a partial front sectional view of FIG. 3. The components of the present invention, which correspond to those of the prior art, are indicated by the same reference numerals.

As shown in FIGS. 3 and 4, a pair of guide rails 22 for guiding the movement of a transducer 10 is disposed near both side-ends of the transducer 10. Slots 24 are formed lengthwise at the side surfaces of the guide rails 22, which are opposite to the both side-ends of the transducer 10. Each slot 24 has a side wall 24a and a bottom wall 24b. The guide rails 22 and the slots 24 may be formed in a convex, linear or concave shape.

Brackets 12, to which bearings 16 are rotatably mounted, are coupled to the both side-ends of the transducer 10. Supporting shafts 14 for supporting the bearings 16 are fixed to the brackets 12. The supporting shafts 14 horizontally extend toward the slots 24 of the guide rails 22 and the bearings 16 are received within the slots 24. The brackets 12 are disposed apart from the side surfaces of the guide rails 22 by predetermined gaps g so as to avoid any undesired friction therebetween.

A device for guiding the movement of a transducer 10 further comprises means for maintaining the gaps g constant between the brackets 12 coupled to the both side-ends of the transducer 10 and the side surfaces of the guide rails 22. The means includes first magnets 42 fixed to the brackets 12 and second magnets 44 fixed to the side walls 24a of slots 24. The first magnets 42 have a size, which is proper to be received in the slots 24, and are positioned near the bearings 16. Preferably, four first magnets 42 are provided symmetrically such that two magnets 42 are fixed to each side-end of the transducer 10. The second magnets 44 are mounted to the side walls 24a of the slots 24 along the overall length of the slots 24. The first magnets 42 and the second magnets 44 are arranged oppositely apart from each other by predetermined gaps g' such that the same poles (N-pole to N-pole, or S-pole to S-pole) face each other to generate the repulsive forces therebetween.

Figure 1:
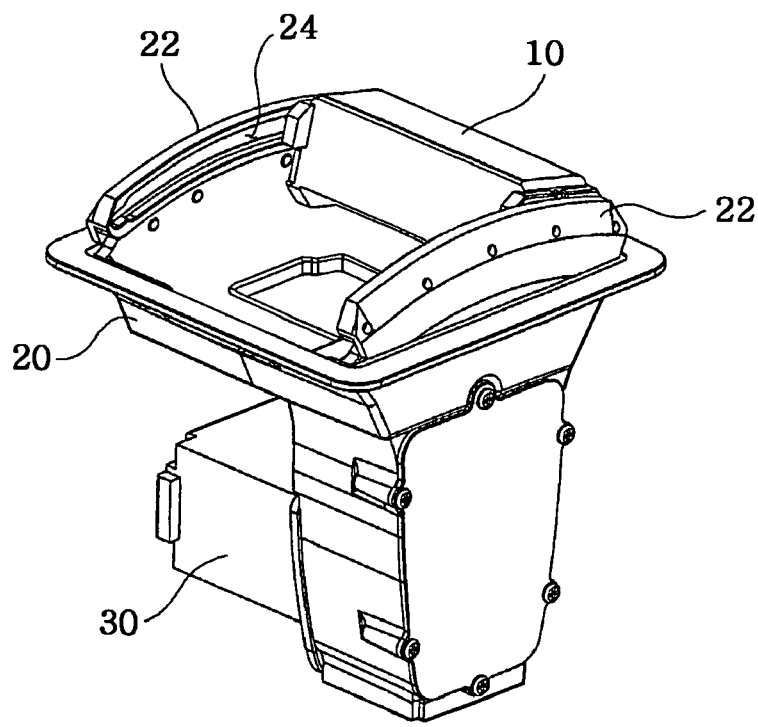
FIG. 1 is a perspective view schematically showing an inner structure of a prior art ultrasonic probe.
Figure 2:
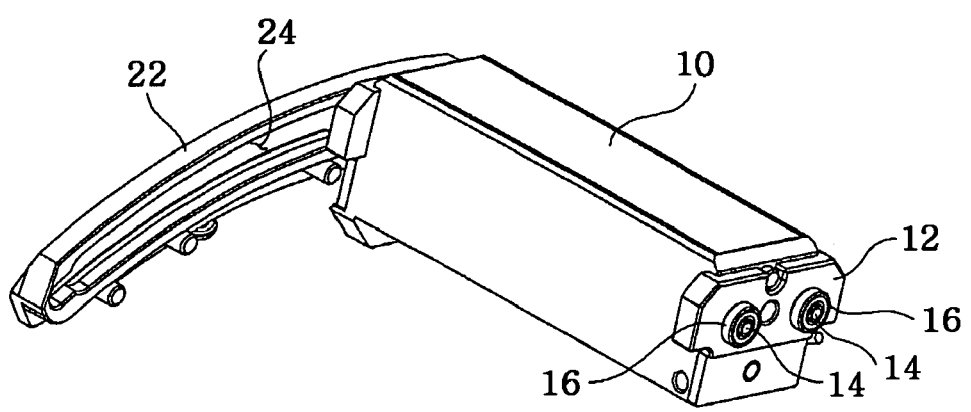
FIG. 2 is a perspective view showing a device for guiding the movement of a transducer of a prior art ultrasonic probe.

When the driving power of a motor 30 (see FIG. 1) is transmitted to the transducer 10 by power-transmitting means, the transducer 10 moves along the guide rails 22 while the bearings 16 roll on the bottom walls 24b of the slots 24. At the same time, the repulsive forces are generated between the N-poles (or the S-poles) of the first magnets 42 and the N-poles (or the S-poles) of the second magnets 44, regardless of the shapes of the guide rails 22 and the slots 24. Because such repulsive forces are generated equivalently near the both side-ends of the transducer 10, the gaps g between the brackets 12 and the side surfaces of the guide rails 22, as well as the gaps g' between the first magnets 42 and the second magnets 44, can be kept constant. As such, the transducer 10 can be prevented from rattling between the pair of guide rails 22 and no friction occurs between the brackets 12 coupled to the both side-ends of the transducer 10 and the side surfaces of the guide rails 22.

Figure 5:
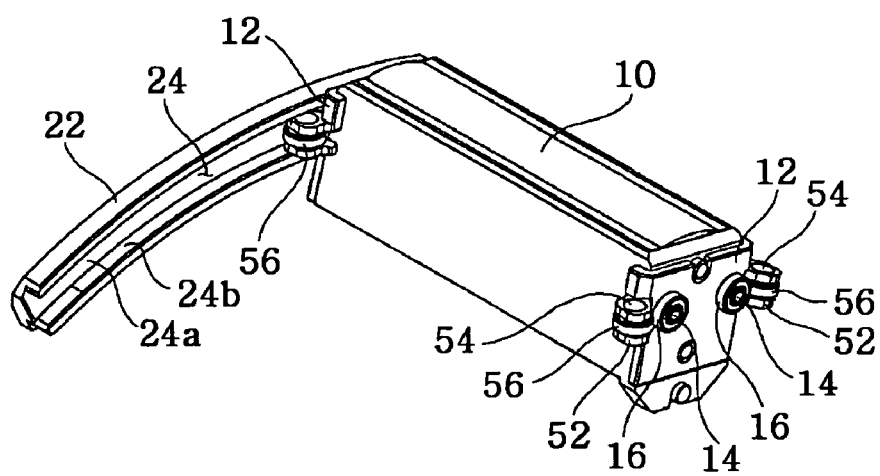
FIG. 5 is a perspective view showing a device for guiding the movement of a transducer of an ultrasonic probe constructed in accordance with another preferred embodiment of the present invention.
Figure 6:
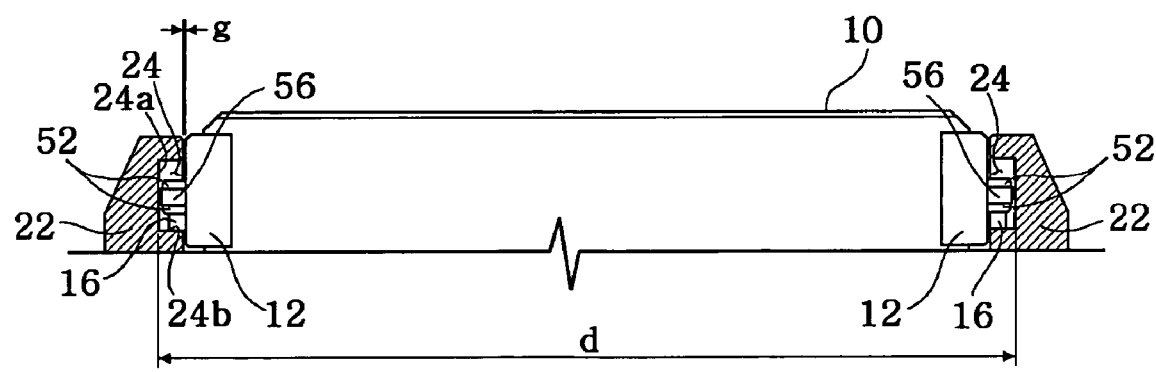
FIG. 6 is a partial sectional view of FIG. 5.

FIG. 5 is a perspective view showing a device for guiding the movement of a transducer of an ultrasonic probe constructed in accordance with another preferred embodiment of the present invention. FIG. 6 is a partial front sectional view of FIG. 5.

As shown in the drawings, the means for keeping the gaps g constant between the brackets 12 coupled to the both side-ends of the transducer 10 and the side surfaces of the guide rails 22 is auxiliary bearings 56, which are additionally mounted to the brackets 12.

More specifically, the existent bearings 16 (hereinafter referred to as "the primary bearings") are disposed such that their rotational axes (i.e., the shafts 14 supporting the primary bearings 16) are horizontally directed toward the side walls 24a of the slots 24. Thus, the primary bearings 16 can support the vertical loads of the transducer 10 and achieve the smooth movement of the transducer 10 by rolling on the bottom walls 24b of the slots 24.

On the other hand, the auxiliary bearings 56 are disposed such that their rotational axes are directed vertically. For supporting the auxiliary bearings 56, there are provided supporting shafts 54, which are disposed vertically. The supporting shafts 54 are fixed to holders 52 formed at the brackets 12. Such auxiliary bearings 56, which have the vertical rotational axes, roll on the side walls 24a of the slots 24. Preferably, four auxiliary bearings 56 are provided symmetrically such that two auxiliary bearings 56 are mounted to each side-end of the transducer 10. The maximum distance d between two points on the peripheries of the auxiliary bearings 56, which are respectively positioned at the both end-sides of the transducer 10, is same as the distance between the side walls 24a of the slots 24 of two opposing guide rails 22.

When the driving power of the motor 30 (see FIG. 1) is transmitted to the transducer 10 by the power-transmitting means, the transducer 10 moves along the guide rails 22 while the primary bearings 16 roll on the bottom walls 24b of the slots 24. At the same time, the auxiliary bearings 56 roll on the side walls 24a of the slots 24, regardless of the shapes of the guide rails 22 and the slots 24. Accordingly, the transducer 10 can be prevented from rattling between the pair of guide rails 22. Further, the gaps g between the brackets 12 coupled to the both side-ends of the transducer 10 and the side surfaces of the guide rails 22 can be kept constant to thereby avoid any undesired friction therebetween.

As described above, during the movement of the transducer, the both side-ends of the transducer (more accurately, the bearing-supporting brackets) can be prevented from contacting the side surfaces of the guide rails by the first and second magnets or the auxiliary bearings, regardless of the shape (convex, linear or concave) of the guide rails. Accordingly, no undesired friction may occur between the bearing-supporting brackets and the guide rails, thereby preventing operational noises or vibrations as well as further preventing wears or deformations of the components. Furthermore, the transducer can move smoothly, thereby increasing the image quality and reducing errors in diagnosis.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A device for guiding the movement of a transducer of an ultrasonic probe, the probe including the transducer for converting an ultrasonic signal into an electric signal and a motor for generating driving power for moving the transducer, the device comprising:

a pair of guide rails disposed adjacent to both side-ends of the transducer, the guide rails being apart from the both side-ends of the transducer by predetermined gaps;

slots formed lengthwise at side surfaces of the guide rails disposed opposite to the both side-ends of the transducer, each slot having a bottom wall and a side wall;

bearings coupled to the both side-ends of the transducer, the bearings being received in the slots and rolling on the bottom walls of the slots; and means for maintaining the gaps constant between the both side-ends of the transducer and the guide rails, wherein the means includes first magnets fixed to the both side-ends of the transducer and second magnets fixed to the side walls of the slots along the overall length of the slots, and wherein the first magnets are received in the slots and are disposed opposite to the second magnets so that repulsive forces are generated therebetween.

2. The device of claim 1, wherein the guide rails and the slots are formed in a shape selected from a group consisting of a convex shape, a linear shape, a concave shape, and combinations thereof.

3. A device for guiding the movement of a transducer of an ultrasonic probe, the probe including the transducer for converting an ultrasonic signal into an electric signal and a motor for generating driving power for moving the transducer, the device comprising:

a pair of guide rails disposed adjacent to both side-ends of the transducer, the guide rails being apart from the both side-ends of the transducer by predetermined gaps;

slots formed lengthwise at side surfaces of the guide rails disposed opposite to the both side-ends of the transducer, each slot having a bottom wall and a side wall;

primary bearings coupled to the both side-ends of the transducer, the primary bearings being disposed such that their rotational axes are horizontally directed, the primary bearings being received in the slots and rolling on the bottom walls of the slots while supporting vertical loads of the transducer; and auxiliary bearings coupled to the both side-ends of the transducer, the auxiliary bearings being disposed such that their rotation axes are vertically directed, the auxiliary bearings being received in the slots and rolling on the side walls of the slots, wherein the auxiliary bearings maintain the gaps constant between the both side-ends of the transducer and the guide rails.

4. The device of claim 3, wherein the guide rails and the slots are formed in a shape selected from a group consisting of a convex shape, a linear shape, a concave shape, and combinations thereof.

* * * * *